USOO5827209A

United States Patent [19]
Gross

[11] Patent Number: 5,827,209
[45] Date of Patent: Oct. 27, 1998

[54] INTELLIGENT BODY SUPPORT

[75] Inventor: Clifford M. Gross, Roslyn, N.Y.

[73] Assignee: BCAM International, Inc., Melville, N.Y.

[21] Appl. No.: 755,199

[22] Filed: Nov. 25, 1996

Related U.S. Application Data

[63] Continuation of Ser. No. 312,093, Sep. 23, 1994, abandoned.

[51] Int. Cl.$^6$ .................................. A61F 5/00; A61B 5/10
[52] U.S. Cl. ................................ 602/19; 602/13; 602/20; 602/23; 602/60; 602/61; 600/595
[58] Field of Search ................................ 602/13, 20, 23, 602/26, 60, 62; 600/595, 587; 607/201, 202, 203

[56] References Cited

U.S. PATENT DOCUMENTS

| | | | |
|---|---|---|---|
| 4,444,205 | 4/1984 | Jackson | 600/595 |
| 4,989,283 | 2/1991 | Krouskop | 5/453 |
| 5,042,504 | 8/1991 | Huberti . | |
| 5,050,618 | 9/1991 | Larsen | 128/774 |
| 5,078,152 | 1/1992 | Bond et al. | 128/774 |
| 5,107,854 | 4/1992 | Knotts et al. . | |
| 5,181,522 | 1/1993 | McEwen | 128/774 X |
| 5,277,197 | 1/1994 | Church et al. | 128/733 |
| 5,360,016 | 11/1994 | Kovacevic | 128/774 X |
| 5,368,546 | 11/1994 | Stark et al. | 428/8 X |

*Primary Examiner*—Richard J. Apley
*Assistant Examiner*—Kim M. Lee
*Attorney, Agent, or Firm*—Snell & Wilmer, L.L.P.

[57] ABSTRACT

An automatic feedback and adjustment setup is integrally connected to a body joint support. The support may be of the flexible, semi-rigid, or rigid type. The support contains one or more inflatable/deflatable bladders, each bladder individually controlled by a hydraulic pump. Sensors embedded in the support monitor muscle activity (EMG) and transmit those electronic measurements to a microprocessor which processes the measurements according to one of a variety of prestored algorithms. The result of this processing is compared to preset minimum and maximum levels. The inflation level of each bladder is then automatically adjusted by activating the hydraulic pumps to keep the calculated level between these preset minimum and maximum. The combination of support, bladders, sensors, microprocessor, comparison device, and hydraulic pumps creates a closed-looped biofeedback system for controlling the degree of joint stress the person is experiencing while wearing the support. Thus, the likelihood of joint, muscular, or soft tissue damage can be minimized. Also disclosed is a method for using the support.

12 Claims, 2 Drawing Sheets

5,827,209

INTELLIGENT BODY SUPPORT

This is a continuation of application Ser. No. 08/312,093 filed Sep. 23, 1994, abandoned.

BACKGROUND OF THE INVENTION

1. Field of the Invention

This invention relates to body joint supports and more particularly to supports utilized to limit joint movement as a preventative against joint injury or as part of treatment for an injured joint.

2. Description of the Prior Art

Body joint supports for the wrist, back, elbow, knee, and other joints are commonly used for providing comfort, completely or partially immobilizing an injured body part while healing, and other cosmetic and orthopedic reasons. The design and availability of various types of supports have come about to meet these various needs.

Supports may be designed for use as either a corrective or preventative measure. A typical corrective support is similar to a cast—immobilizing an injured joint during the healing process. The majority of supports available today are designed for use as a corrective measure.

A typical example of the "corrective" support is disclosed in U.S. Pat. No. 4,175,553 issued on Nov. 27, 1979 to H. W. Rosenberg for a lumbosacral-orthosis orthopedic support incorporating rigid metal plates. This invention is for use by persons who are physically incapable of performing lifting and other strenuous material handling tasks. The patent discloses a device which braces and supports an injured back or spine against unwanted movement which, if not prevented, could result in severe pain and further injury. This support attempts to minimize back movement.

There is, however, a growing minority of supports that are designed for use as a preventative measure. For example, a typical preventative support may transmit stresses in the user's body from one body region to another such as from the lumbar area to the pelvic area. This transfer may be accomplished by an arrangement of specially designed stays or plates located within the support. A support of this design allows the wearer to perform required occupational functions or other functions which include twisting or bending of the body.

An illustration of the "preventative" support is disclosed in U.S. Pat. No. 4,553,551 issued on Nov. 19, 1985 to Clifford M. Gross. This invention is for use by persons who are physically capable of performing lifting and other strenuous material handling tasks. The patent discloses a body-encircling lifting belt with a permanently fixed configuration of metal stays. It operates by transferring stress from the lumbar body area to the pelvic body area and also provides torsional rigidity for the user's torso. By these actions, the user is induced to bend at a slower rate and not excessively twist the torso. Thereby, the possibility of back injury is reduced.

Pain is the body's natural feedback warning signal to alert a person to movements that exceed that body's tolerance and may result in injury. However, it is well-known that a person may suffer debilitating consequences from the cumulative effects of repetitive stresses from movements during which the person does not feel any pain. Thus, it is desirable to have a mechanism by which joint stresses are continually and automatically monitored and controlled to remain within acceptable limits while the joint is being stressed. Thereby, one can avoid injury due to excessive stresses on body joints while the joint is being stressed, whether or not the person experiences pain at that time.

Consequently, the above examples depict a major shortcoming of the prior art. It is true that, by careful initial selection of the material, size, quantity, and layout of the stays in a body joint support, a medical professional should be able to create meaningful resistance to a person's attempts to move designated body joints in ways and to extents which are not safe for that person. However, there is no way to monitor whether the resistance is sufficient to contain this particular person's movement within limits desired by the medical professional. Furthermore, the person may look towards feelings of "pain" to provide an indication of when the limits have been reached; as discussed above, the sensation of "pain" may come too late to prevent injury. Thus, even with careful up-front planning, the supports may, during use, fail to prevent movement that is in excess of what is safely tolerable for the particular person. Clearly, the user does not have ready access to quantitative analysis of the joint stress being experienced. Thus, joint injury from the cumulative effects of stress can result unknowingly.

SUMMARY OF THE INVENTION

A primary object of this instant invention is a system to automatically adjust the support provided by a body support while in use based upon the relative level of stress in a particular body joint due to ongoing movement.

Another object of this invention is a system to automatically control the relative level of stress in a particular body joint.

Still another object of this invention is a system to automatically maintain the level of stress in a particular body joint within a range established by a medical professional.

In short, this invention is an automatic feedback and adjustment setup integrally connected to a body joint support. The support may be of the flexible, semi-rigid, or rigid type. The support contains one or more inflatable/deflatable bladders, each bladder individually controlled by a hydraulic pump. Sensors embedded in the support monitor muscle activity (EMG) and transmit those electronic measurements to a microprocessor which processes the measurements according to one of a variety of prestored algorithms. The result of this processing is compared to preset minimum and maximum levels. The inflation level of each bladder is then automatically adjusted by activating the hydraulic pumps to keep the calculated level between these preset minimum and maximum.

The combination of support, bladders, sensors, microprocessor, comparison device, and hydraulic pumps creates a closed-looped biofeedback system for controlling the degree of joint stress the person is experiencing while wearing the support. Thus, the likelihood of joint, muscular, or soft tissue damage can be minimized.

DESCRIPTION OF PREFERRED EMBODIMENT

Figure 1:
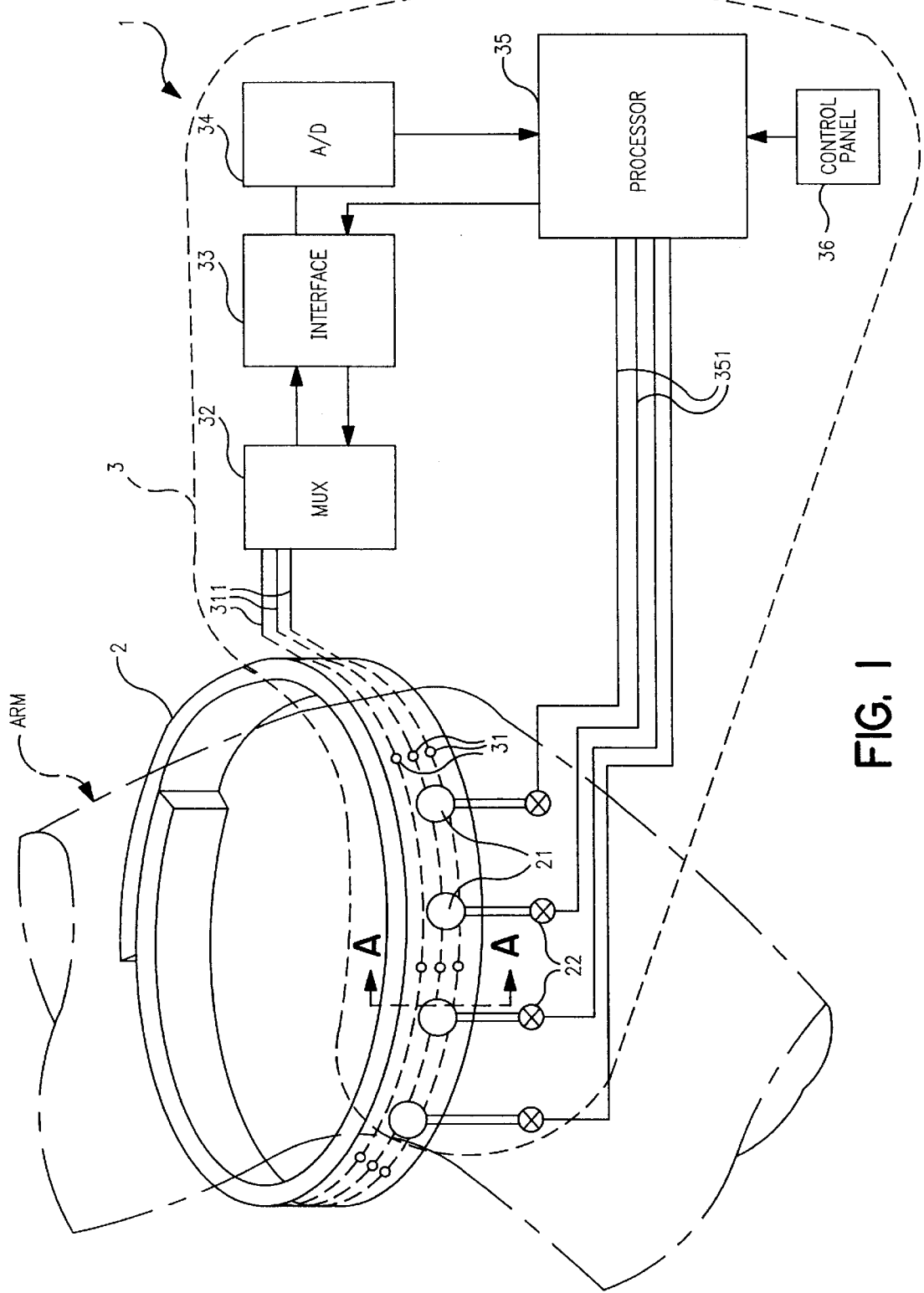
FIG. 1 is a schematic drawing of the body support and automatic adjustment system for an arm elbow joint.
Figure 2:
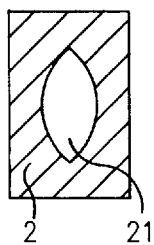
FIG. 2 is a cross-section of the body support shown in FIG. 1 along line A—A.

In its preferred embodiment, this invention comprises a body joint support system 1 for use with a body joint such as a wrist, spine, elbow ankle, or knee. The support system 1 comprises a joint support 2 and an automatic feedback and control system 3 for controlling the level of support provided by the support 2 based upon the extent of motion through which the user is putting the supported joint.

The support 2 can be of the flexible, semi-flexible, or rigid variety; these varieties are well-known in the prior art. A typical support material is elastic. The actual design of a support varies depending upon the joint for which that support is intended. However, the basic features for all supports are very similar and a single representative support can be used to describe the structure and workings of all the supports.

The automatic feedback and control system 3 comprises one or more sensors 31 that are removably placed within the support 2, just beneath the surface of the support which makes contact with the user's joint. Sensors 31 may advantageously comprise any prior art sensor and, in particular, preferably comprise sensors that measure muscle activity using surface electrodes and solid state amplifiers to amplify the signals obtained from these surface electrodes. The sensors 31 may be selected from one or more of the well-known sensor types that measure skin pressure (e.g. pressure exerted on the skin, or exerted by the skin on the support), joint motion, strain, and joint velocity and the like. Illustratively, each of the pressure sensors 31 is a Force Sensing Resistor available from Interlink Electronics, Santa Barbara, Calif. These devices are polymer thick film devices which exhibit a decreasing resistance when an increasing force is applied in a direction normal to the device surface.

The feedback system 3 further comprises one or more inflatable/deflatable bladders 21 that are integral with the support 2. These bladders 21 are preferably similar to the well-known bladders used in blood pressure cuffs, but whose shape and number are dictated by the particular joint being supported. The bladders 21 are individually connected to air pumps 22 so that each bladder 21 can be independently inflated or deflated as needed. Preferably, the pumps 22 are completely portable, so that the user's movement is not restricted to a particular physical area. Such pumps 22 are well-known in the prior art.

The remainder of the feedback system 3 includes a multiplexer 32, an interface 33, an analog-to-digital converter 34, a microprocessor 35, and pump signal lines 351. The multiplexer 32 connects a signal 311 from any one of the sensors 31 to the interface 33. The sequence in which the sensors 31 are to be interrogated is transmitted from the microprocessor 35 to the interface 33. Analog signals 311 from the multiplexer 32 are transmitted through the interface 33 to the analog-to-digital converter 34 wherein the signals 311 from the sensors 31 are converted to digital form and transmitted to the microprocessor 35 which stores these signal values in memory. All of these components are well-known in the prior art.

Figure 3:
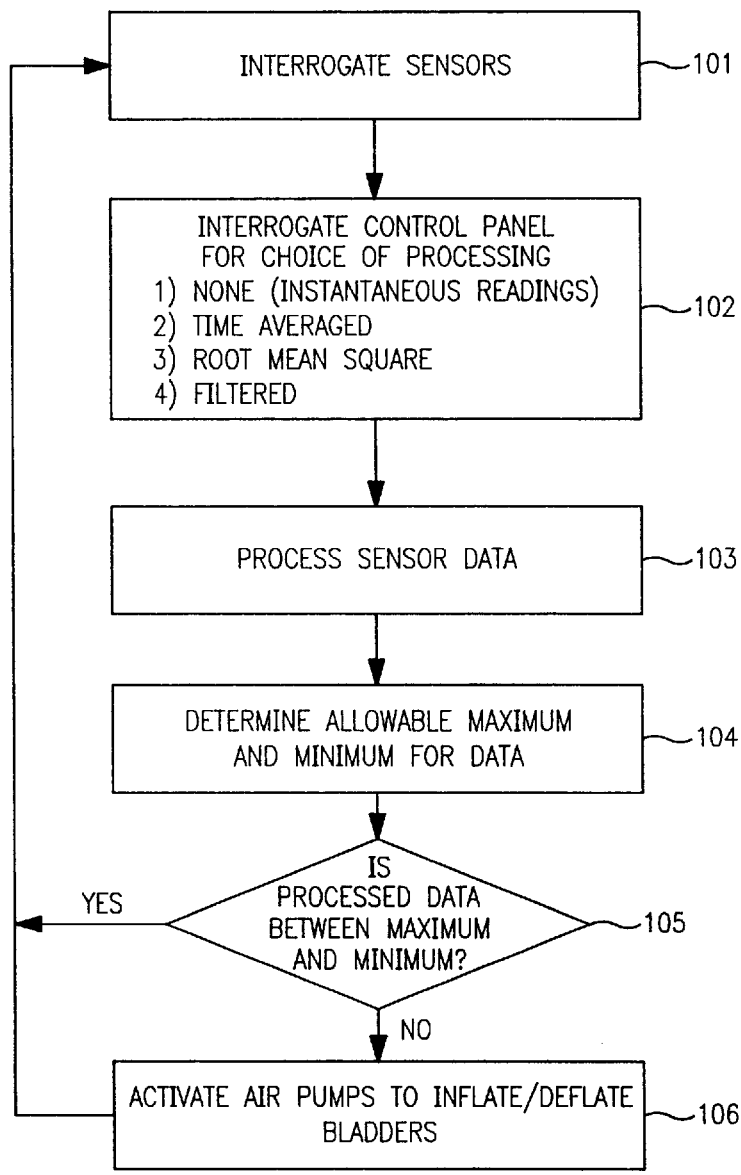
FIG. 3 is a flow chart schematically illustrating an algorithm carried out by the microprocessor in the system shown in FIG. 1.

An illustrative algorithm utilized by the microprocessor 35 to process the signals and produce an indication of the joint stress level is illustrated by the flow chart of FIG. 3. Thus, as shown in FIG. 3, the first step of the stress indication process is to interrogate the sensors 31 (box 101) to obtain data representative of the actual movement of the supported joint. Because the stress indication output operates continually, this data may be time averaged, filtered, or subjected to root-mean-square analysis before producing output (box 103). Thus, the second step of the process is to interrogate the microprocessor control panel 36 (box 102) to determine whether the user or medical professional has selected any of these options.

Instead of using the foregoing algorithm, the microprocessor 35 may evaluate a more complex algorithm. For example, an actual stress level of a joint may be set equal to a linear combination of a variety of the different sensor measurements previously mentioned and/or a variety of the available output forms previously mentioned. When a linear combination of such values, representing a joint stress level, is obtained, the microprocessor 35 compares this joint stress level to an preset acceptable stress level range. The microprocessor 35 then provides output over the pump signal lines 351 to control the pumps 22 (boxes 105, 106).

Thus, when the joint being monitored is moved within the support 2, the microprocessor 35 receives from the sensors 31 data representative of the actual motion of the joint (for example, extent, speed, torsion, or flexion). This data is processed by the microprocessor 35 and, in response to this data, the microprocessor 35 determines whether the processed data reflects a value that is within preset acceptable limits (boxes 104, 105). If the limits have been exceeded, the microprocessor 35 activates the air pumps 22 inflating or deflating individual bladders 21, as needed (box 106). In this manner, as the user moves the supported joint, the amount of support is constantly adjusted based upon the then current state of the joint, thereby maintaining the stress on the joint within these preset acceptable limits and avoiding potential injuries to the joint.

Prior to use, a medical professional determines an acceptable range of motion or stress that the particular body joint can tolerate to minimize the risk of injury due to cumulative stress exposure of that joint. This range can be derived based on conventional statistical techniques or in other ways well-known in the prior art, and may be adjusted for the individual user.

In use, that acceptable motion or stress range is entered into the microprocessor 35 via the microprocessor control panel 36 or by some other well-known method.

The user or medical professional then chooses a desired monitoring analysis form by pressing a button on the control panel 36. Analysis forms preferably include instantaneous readings, time-averaged, root-mean square, and filtered; all of these forms are well-known in the prior art. The user next attaches the support 2 around the body joint and begins to move the joint.

Each sensor 31 responds to the movement by detecting the activity corresponding to its intended purpose and producing a corresponding analog signal 311. The analog signals 311 produced by all the sensors 31 are then passed through an amplifier (not shown). These amplified signals are then sent to a microprocessor 35 via the pathway established by the multiplexer 32, interface 33, and an analog-to-digital converter 34. By the end of the pathway, the analog signals 311 have been converted into digital signals. This conversion process is well-known in the prior art. These digital signals then enter the microprocessor 35.

The microprocessor 35 utilizes the digital signals as follows. First, the microprocessor 35 polls the control panel 36 to see which output form has been chosen. The microprocessor 35 then processes the digital signals, utilizing well-known microprocessor algorithms, to produce the chosen analysis form. The microprocessor 35 then begins the polling-processing process anew; thereby producing a continual analysis stream.

The microprocessor 35 now determines if at any instant, the analysis stream is within desired limits. If so, no action occurs. If not, the microprocessor 35, via signals over the lines 351, activates the pumps 22 that inflate and/or deflate individual bladders 21 to adjust the stress on the supported joint. Thus a closed-loop feedback system is established comprising (a) the support 2; (b) the bladders 21; (c) the pumps 22; (d) the sensors 31; (e) the microprocessor 35; and (f) the pump control lines 351, which close the loop.

Consequently, as the user continues to move the monitored joint, the amount of support provided to that joint is continually and automatically adjusted. Thereby, dangerous levels of stress are avoided in the monitored joint with minimum inconvenience to the user.

Although this invention has been described with a certain degree of particularity, it is to be understood that the present disclosure has been made only by way of illustration and that numerous changes in the details of construction and arrangement of parts may be resorted to without departing from the spirit and scope of this invention. For example, the bladders 21 and pumps 22 may be replaced with other combinations of mechanical stiffening devices, which are well-known in the prior art. Further, the need to use bladders 21 and pumps 22 may be completely eliminated if the support 2 comprises a material whose stiffness is changeable through the application of electrical signals or fields; in this instance, the lines 351 would simply run directly from the microprocessor 35 to the support 2.

Also, the static preset limits on joint stress may be replaced with a more complex program that changes these limits with respect to elapsed time, cumulative stress, or other dynamic variables. In this instance, it is preferred that the microprocessor 35 further comprise downloading means to allow for easy entry of the limit-calculating program; such downloading means are well-known in the prior art.

I claim:

1. An apparatus for automatically monitoring and controlling a relative level of movement within a body joint, comprising:
    a joint support configured for contact with at least a portion of the body joint, the support comprising;
        at least one inflatable bladder configured to apply variable pressures to predetermined areas of the body joint;
        a plurality of sensors, integrally placed on a plurality of predetermined locations of the joint support and in contact with predetermined positions on the body joint, said sensors being configured to monitor movement of the body joint in the region of said predetermined locations over a variety of angular orientations with respect to said support through a range of motion of the body joint;
        said sensors being further configured for establishing and sending an electronic signal representing said monitored movement of the body joint;
    a processor electronically connected to said sensors, said processor configured to receive and convert said electronic signals from said sensors into a joint movement value, compare said joint movement value to predetermined joint movement values selected such that the body joint is supported through a range of motion of the body joint; and
    a pressure control device connected to said processor and said at least one inflatable bladder, said pressure control device adjusting pressure within said at least one inflatable bladder to substantially maintain said predetermined joint movement value.

2. Apparatus as described in claim 1 in which:
    (a) the pressure control device comprises a pump; and
    (b) the pressure control device comprises pump control means to control the pump, thereby adjusting the level of inflation; the pump control means being electronically connected to the processor and the pump.

3. Apparatus as described in claim 1 in which:
    (a) the joint support and at least one inflatable bladder comprise a material having a stiffness that is controllable by the application of an electrical signal or field; and
    (b) the pressure control device comprises material control means to apply the electrical signal or field to the material, thereby adjusting the stiffness of the material; the material control means being electronically connected to the processor and the material.

4. Apparatus as described in claim 1 in which the joint movement value comprises a root mean square representation of the electronic signals from the sensors.

5. Apparatus as described in claim 1 in which the joint movement value comprises a filtered representation of the electronic signals from the sensors.

6. Apparatus as described in claim 1 in which the joint movement value comprises a filtered representation of the electronic signals from the sensors.

7. Apparatus as described in claim 1 in which the predetermined joint movement values comprise a maximum joint movement value and a minimum joint movement value.

8. Apparatus as described in claim 1 in which said sensors are further configured to measure skin pressure proximate said body joint.

9. Apparatus as described in claim 1 in which said sensors are further configured to measure strain in said body joint.

10. Apparatus as described in claim 1 in which said sensors are further configured to measure joint velocity.

11. Apparatus of claim 1 in which the pressure applied to the body joint comprises a predetermined pressure required to adequately support the body joint and concurrently allow permissible body joint movement.

12. A method of automatically controlling a relative level of motion in a body joint, utilizing a joint support being placeable in contact with the body joint, the support exerting a pressure against the body joint during movement of the body joint, the support being automatically adjustable to vary the pressure; the method comprising:
    (a) establishing an upper limit of desired motion and a lower limit of desired motion for the body joint during movement of the body joint;
    (b) creating an acceptable range of motion for the body joint bounded by the upper limit and the lower limit;
    (c) making a measurement of signals from a plurality of sensors distributed within the joint support across the body joint, the signals being representative of the movement of the body joint at a specific time;
    (d) processing the signals to form a data value representative of the position of the body joint at the specific time;
    (e) determining whether the position of the body joint, as represented by the data value, is within the acceptable range of motion; and
    (f) if the data value does not represent an acceptable position of the body joint, automatically adjusting the pressure such that movement of the body joint is within the range of motion.

* * * * *